United States Patent
Nelson et al.

(10) Patent No.: US 8,485,725 B2
(45) Date of Patent: Jul. 16, 2013

(54) SYSTEM AND METHOD FOR DETECTING AN UNEXPECTED MEDIUM OR A CHANGE OF MEDIUM SENSED BY A THERMISTOR

(75) Inventors: Brian Carl Nelson, Bath, MI (US); Marilyn L. Kindermann, Milford, MI (US); Brian K. Kowalczyk, Howell, MI (US); Christian G. Masson, Howell, MI (US)

(73) Assignee: GM Global Technology Operations LLC

( * ) Notice: Subject to any disclaimer, the term of this patent is extended or adjusted under 35 U.S.C. 154(b) by 273 days.

(21) Appl. No.: 12/974,299

(22) Filed: Dec. 21, 2010

(65) Prior Publication Data

US 2012/0155506 A1     Jun. 21, 2012

(51) Int. Cl.
*G01K 7/00*    (2006.01)
*G01N 25/00*   (2006.01)

(52) U.S. Cl.
USPC ............................................. 374/185; 374/43

(58) Field of Classification Search
USPC .................................................. 374/185, 43
See application file for complete search history.

(56) References Cited

U.S. PATENT DOCUMENTS

| | | | | |
|---|---|---|---|---|
| 5,335,513 | A  | * | 8/1994 | Campbell et al. ............ 62/228.3 |
| 5,660,052 | A  | * | 8/1997 | Kenyon et al. ............... 62/228.3 |
| 7,104,684 | B2 | * | 9/2006 | Felder ........................... 374/178 |
| 7,653,503 | B2 | * | 1/2010 | Mangalam et al. ........... 702/100 |
| 2007/0122173 | A1 | * | 5/2007 | Mitsuoka et al. ............... 399/69 |
| 2007/0160108 | A1 | * | 7/2007 | Kent ................................ 374/54 |
| 2011/0106476 | A1 | * | 5/2011 | Son et al. ........................ 702/99 |
| 2012/0062041 | A1 | * | 3/2012 | Nelson et al. ................. 307/116 |

OTHER PUBLICATIONS

U.S. Appl. No. 12/882,448, filed Sep. 15, 2010, Brian Carl Nelson et al.

* cited by examiner

*Primary Examiner* — Mirellys Jagan

(57) ABSTRACT

A system for detecting a change in medium sensed by a thermistor comprises a first module that receives a temperature signal from a thermistor and that calculates a first dissipation factor of the thermistor. A second module receives the first dissipation factor of the thermistor and detects at least one of an unexpected medium and a change in medium based on the first dissipation factor.

12 Claims, 3 Drawing Sheets

SYSTEM AND METHOD FOR DETECTING AN UNEXPECTED MEDIUM OR A CHANGE OF MEDIUM SENSED BY A THERMISTOR

FIELD

The present disclosure relates to temperature sensing, and more particularly to systems and methods for detecting an unexpected medium or a change in medium sensed by a thermistor.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Thermistors are thermally sensitive resistors having a resistance that changes with temperature. Changes in the resistance of the thermistor can occur in several ways. For example, the resistance may change due to changes in ambient temperature. In addition, the resistance of the thermistor changes due to self-heating caused by current flowing through the thermistor. Current flowing through the thermistor may cause sufficient heating to raise the temperature above the ambient temperature. Self-heating depends on a load that is applied, a thermal dissipation factor ($\delta$th) and a geometry of the thermistor.

SUMMARY

A system for detecting changes in a medium sensed by a thermistor comprises a first module that receives a temperature signal from a thermistor and that calculates a first dissipation factor of the thermistor. A second module receives the first dissipation factor of the thermistor and detects at least one of an unexpected medium and a change in medium based on the first dissipation factor.

In other features, the second module determines whether the first dissipation factor is within a predetermined range. The second module detects the unexpected medium when the first dissipation factor is outside of the predetermined range.

In other features, the first dissipation factor is compared to a second dissipation factor that is calculated by the second module before the first dissipation factor. The second module detects the change in medium when a difference between the first and second dissipation factors is greater than a predetermined difference.

In other features, the first module performs temperature compensation on the temperature signal based on the dissipation factor. A component control module controls a component. The component control module adjusts operation of the component when the at least one of the unexpected medium and the change of medium is detected.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
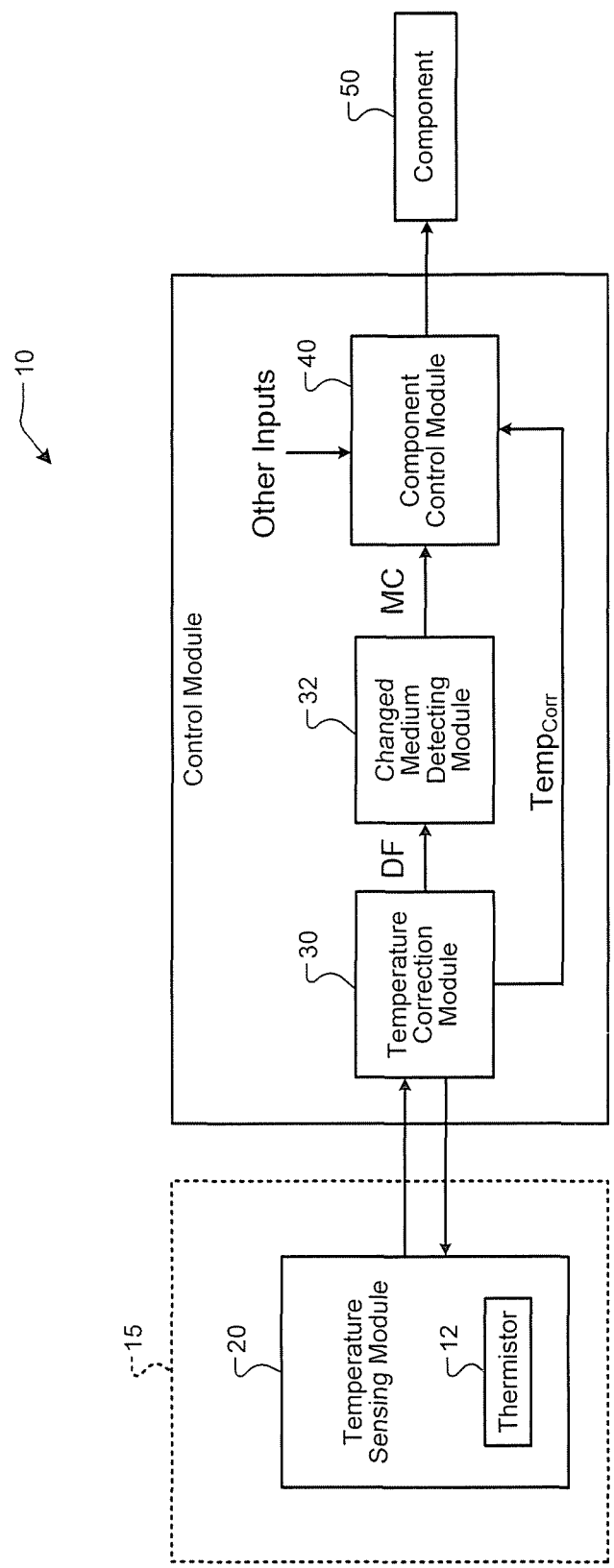
FIG. 1 is a functional block diagram of an example system for detecting an unexpected medium or a change in a medium sensed by a thermistor according to the present disclosure.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure determines whether or not a medium that the thermistor is sensing is an unexpected medium or has changed. The present disclosure identifies the unexpected medium or changes of a medium sensed by a thermistor based on a dissipation factor of the thermistor. Using the dissipation factor for detecting an unexpected medium or changes of the medium allows for a relatively fast response time.

Some conventional systems detect changes of the medium sensed by the thermistor by sensing whether the medium (that the thermistor is operating in) is moving or still. Most require additional hardware such as an additional dedicated sensor (which increases cost). Alternately, some systems require the thermistor to be positioned in a suboptimal location.

For example, in an automobile it is desirable to know if the engine coolant has leaked, which leads to overheating of the engine. Often this knowledge is gained by using a dedicated hot metal sensor (which adds cost). Alternately, an existing coolant temperature sensor can be located near the exhaust, which will heat the air (which has replaced the coolant) quickly enough to sense the loss of coolant. In order to take protective action before damage occurs, the present disclosure can detect the loss of coolant without the need for an additional dedicated sensor and/or having to locate the coolant temperature sensor in a sub-optimal location.

One system and method for determining the dissipation factor is disclosed in "SYSTEM AND METHOD FOR MORE ACCURATE TEMPERATURE SENSING USING THERMISTORS", U.S. patent application Ser. No. 12/882, 488, filed on Sep. 15, 2010, which is hereby incorporated by reference in its entirety. The dissipation factor is calculated and used to compensate temperature readings. Typical values for a small glass bead thermistor are 1.5 mW/° C. in still air and 6.0 mW/° C. in stirred oil. However, other systems and methods for determining the dissipation factor can be used.

Referring now to FIG. 1, an example of a system 10 that corrects a temperature sensed by a thermistor 12 is shown. The system 10 includes a temperature sensing module 20, a temperature correction module 30, a changed medium detecting module 32, a component control module 40, and a component 50. The temperature sensing module 20 senses a temperature of a target environment 15 using the thermistor 12. For example, the thermistor 12 may include a negative temperature coefficient (NTC) or a positive temperature coefficient (PTC) thermistor. Additionally, for example, the thermistor 12 may include a semiconductor-based thermistor, a ceramic-based thermistor, or a polymer-based thermistor. The thermistor 12, however, may include a different type of thermistor and/or include different materials.

The temperature correction module 30 communicates with the temperature sensing module 20. Specifically, the temperature correction module 30 may determine parameters corresponding to the thermistor 12 by changing a resistance in series with the thermistor 12. Additionally, the temperature correction module 30 receives a signal from the temperature sensing module 20 indicating a temperature sensed by the thermistor 12. The temperature correction module 30 corrects the sensed temperature by compensating for self-heating effects of the thermistor 12. The temperature correction module 30 generates a signal indicating a corrected temperature $Temp_{corr}$.

The changed medium detecting module 32 receives the dissipation factor (DF) and selectively determines when the medium has been changed. The changed medium detecting module 32 may generate a medium changed (MC) signal that has one state when the sensed medium changes and another state when the sensed medium has not changed.

The component control module 40 receives the MC and $Temp_{corr}$ signals from the temperature correction module 30. In some implementations, the DF signal may also be provided to the component control module 40. The component control module 40 controls one or more components 50 based on the DF, $Temp_{corr}$, and/or the MC signals.

For example, the component 50 may include any suitable component in a temperature-based system (i.e., a component having a temperature-based input). In other words, the component control module 40 may more accurately control the component 50 based on the corrected temperature. For example, the system 10 may be implemented in an engine system and the component control module 40 may control at least one component of the engine system. The medium may comprise oil, air, coolant and/or other fluids.

More specifically, the system 10 may correct temperatures from one or more temperature sensors in the engine system. For example, the engine system may include an intake air temperature (IAT) sensor, an engine coolant temperature (ECT) sensor, and/or a transmission fluid temperature (TFT) sensor. The system 10, however, may also correct temperatures of other temperature sensors in the engine system. The corrected temperatures may then be used to control one or more components of the engine system. For example only, the component control module 40 may control a transmission, an engine and/or a heating, ventilating, and air conditioning (HVAC) system based on the corrected temperature.

Figure 2:
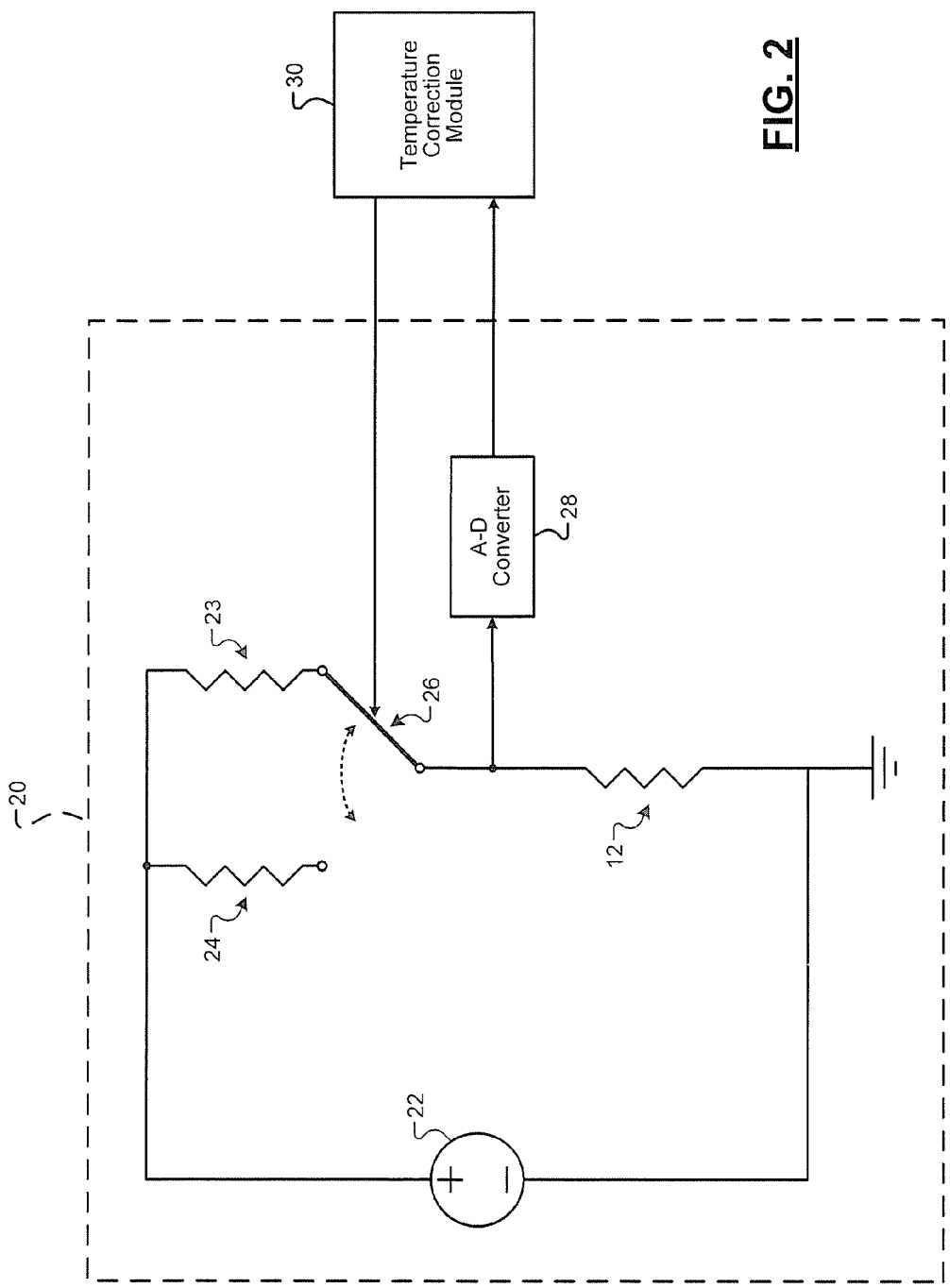
FIG. 2 is a schematic of an example temperature sensing module.

Referring now to FIG. 2, an example of the temperature sensing module 20 is shown in more detail. The temperature sensing module 20 includes a voltage source 22, a first resistor 23, a second resistor 24, a switch 26, the thermistor 12, and an analog-to-digital (A-D) converter 28. Specifically, the switch 26 may select the first resistor 23 or the second resistor 24 to be connected in series with the thermistor 12. For example, the switch 26 may be electrically controlled by the temperature correction module 30. The A-D converter 28 may convert a voltage between the switch 26 and the thermistor 12 to an electrical signal for the temperature correction module 30. For example, the electrical signal may be used to determine the temperature sensed by the thermistor 12 and/or the parameters of the thermistor 12.

More specifically, the parameters of the thermistor 12 include first and second temperatures of the thermistor 12 ($T_1$ and $T_2$, respectively) and first and second power dissipation values of the thermistor 12 ($P_1$ and $P_2$, respectively). The temperature correction module 30 determines the parameters $T_1$, $T_2$, $P_1$, and $P_2$ based on the known voltage ($V_S$) from the voltage source 22 and the known resistances of resistors 23, 24 ($R_1$ and $R_2$, respectively). For example, the resistances $R_1$ and $R_2$ may be predetermined and stored in memory. Additionally, for example, the temperature correction module 30 may include a first module that determines parameters $T_1$ and $P_1$ and a second module that actuates the switch 26 and determines parameters $T_2$ and $P_2$.

First, the switch 26 may be actuated to connect the first resistor 23 in series with the thermistor 12. A voltage drop across the first resistor 23 may be determined as follows:

$$V_{R1} = V_S - V_T \quad (1),$$

where $V_{R1}$ represents the voltage drop across the first resistor 23, $V_S$ represents the source voltage, and $V_T$ represents a voltage drop across the thermistor 12 (i.e., $V_T = V_S - V_{R1}$).

The current through the first resistor 23 may then be determined as follows:

$$I_{R1} = V_{R1}/R_1 \quad (2),$$

where $I_{R1}$ represents the current through the first resistor 23 and $R_1$ represents the known resistance of the first resistor 23. A resistance of the thermistor 12 ($R_T$) may be determined as follows:

$$R_T = V_T/I_{R1} \quad (3).$$

The first temperature $T_1$ of the thermistor 12 may then be determined based on the resistance $R_T$. For example, the first temperature $T_1$ may be determined using a characteristic math equation or lookup table relating various resistances to corresponding temperatures. Additionally, the first power dissipation value $P_1$ of the thermistor 12 may be determined as follows:

$$P_1 = V_T \times I_{R1} \quad (4).$$

After the first temperature $T_1$ and the first power dissipation value $P_1$ are determined, the switch 26 may be switched to connect the second resistor 24 in series with the thermistor 12. A voltage drop across the second resistor 24 may be determined as follows:

$$V_{R2} = V_S - V_T \quad (5)$$

where $V_{R2}$ represents the voltage drop across the second resistor 24, $V_S$ represents the source voltage, and $V_T$ represents the voltage drop across the thermistor 12.

The current through the second resistor 24 may then be determined as follows:

$$I_{R2} = V_{R2}/R_2 \quad (6),$$

where $I_{R2}$ represents the current through the first resistor 23 and $R_2$ represents the known resistance of the second resistor 24. The resistance of the thermistor 12 $R_T$ may the again be determined as follows:

$$R_T = V_T/I_{R2} \quad (7),$$

where $V_T$ represents the voltage drop across the thermistor 12 (i.e., $V_T = V_S - V_{R1}$).

The second temperature $T_2$ of the thermistor 12 may then be determined based on the resistance $R_T$. For example, the second temperature $T_2$ may be determined by the characteristic math equation or using the lookup table relating various resistances to corresponding temperatures. Additionally, the second power dissipation value $P_2$ may be determined as follows:

$$P_2 = V_T \times I_{R2} \quad (8).$$

After the parameters $T_1$, $T_2$, $P_1$, and $P_2$ are determined, the temperature correction module 30 may determine the thermal dissipation factor ($\delta_T$) of the thermistor 12 based on the parameters. Specifically, the thermal dissipation factor $\delta_T$ may be determined as follows:

$$\delta_T = |P_2 - P_1|/|T_1 - T_2| \quad (9).$$

The temperature correction module 30 may then determine a temperature error ($T_E$) based on the thermal dissipation factor $\delta_T$. Specifically, the temperature error $T_E$ may be determined as follows:

$$T_E = P/\delta_T \quad (10),$$

where P represents a power dissipation value of the thermistor 12.

Finally, the temperature correction module 30 may correct the temperature sensed by the thermistor ($T_M$) based on the temperature error. Specifically, the corrected temperature ($T_c$) may be determined as follows:

$$T_C = T_M - T_E \quad (11),$$

where $T_M$ represents the temperature sensed (i.e., measured) by the thermistor 12. Additionally, the process of determining the temperature error $T_E$ and correcting the temperature (see Equations 1-11) may be repeated as often as necessary. For example, the process may be repeated when conditions change (i.e., ambient temperature changes by more than a predetermined temperature threshold).

As can be appreciated, the particular manner of calculating the dissipation factor (DF) and corrected temperature can be performed in any suitable manner and is not limited to the particular example set forth above.

Figure 3:
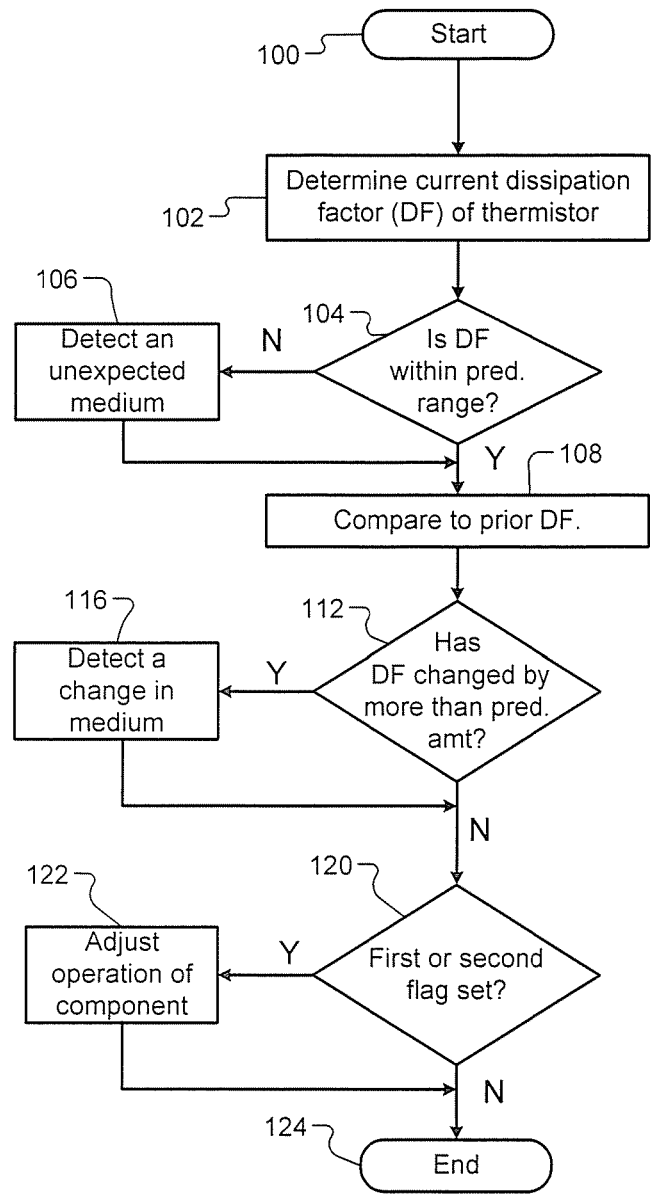
FIG. 3 is an example flow diagram of a method to detect—an unexpected medium or a change in a medium according to the present disclosure.

Referring now to FIG. 3, control begins at 100. At 102, the current dissipation factor (DF) of the thermistor is determined. At 104, control determines whether the current dissipation factor is within a predetermined range. If 104 is false, control sets a first signal to a state corresponding to detection of an unexpected medium at 106. Control continues from 104 (when true) and from 106 with 108.

At 108, control compares the current dissipation factor to a prior dissipation factor. At 112, control determines whether the current dissipation factor has changed by more than a predetermined amount. If 112 is true, control continues at 116, sets a second signal to a state corresponding to detection of a change in medium, and control continues at 120. If 112 is false, control continues at 120 and determines whether the first or second signals were set to states corresponding to detection of an unexpected medium or a changed medium. If the 120 is true, control selectively adjusts operation of the component, sets other flags or takes other action at 122. Control ends at 124. As can be appreciated, events such as overheating or improper coolant types may be identified based on the first signal and/or the second signal.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A system for detecting an unexpected medium or a change in medium sensed by a thermistor, comprising:
    a first module that receives a temperature signal from a thermistor and that calculates a first dissipation factor of the thermistor; and
    a second module that receives the first dissipation factor and that detects at least one of an unexpected medium and a change in medium based on the first dissipation factor,
    wherein the first dissipation factor is compared to a second dissipation factor that is calculated by the first module before the first dissipation factor.

2. The system of claim 1, wherein the second module detects the change in medium when a difference between the first and second dissipation factors is greater than a predetermined difference.

3. The system of claim 1, wherein the first module performs temperature compensation on the temperature signal based on the dissipation factor.

4. The system of claim 1, further comprising a component control module that controls a component, wherein the component control module adjusts operation of the component when the at least one of the unexpected medium and the change of medium is detected.

5. The system of claim 1, wherein the second module determines whether the first dissipation factor is within a predetermined range.

6. The system of claim 5, wherein the second module detects the unexpected medium when the first dissipation factor is outside of the predetermined range.

7. A method for detecting a change in medium sensed by a thermistor, comprising:
    receiving a temperature signal from a thermistor;
    calculating a first dissipation factor of the thermistor;
    detecting at least one of an unexpected medium and a change in medium based on the first dissipation factor; and
    comparing the first dissipation factor to a second dissipation factor that is calculated before the first dissipation factor.

8. The method of claim 7, further comprising detecting the change in medium when a difference between the first and second dissipation factors is greater than a predetermined difference.

9. The method of claim 7, further comprising performing temperature compensation on the temperature signal based on the dissipation factor.

10. The method of claim 7, further comprising adjusting operation of a component when the at least one of the unexpected medium and the change of medium is detected.

11. The method of claim 7, further comprising determining whether the first dissipation factor is within a predetermined range.

12. The method of claim 11, further comprising detecting the unexpected medium when the first dissipation factor is outside of the predetermined range.

* * * * *